United States Patent [19]

Gersonde et al.

[11] Patent Number: 4,469,439
[45] Date of Patent: Sep. 4, 1984

[54] PROCESS AND APPARATUS FOR PLOTTING THE OXYGEN EQUILIBRIUM CURVES OF BLOOD OR HEMOGLOBIN SOLUTIONS

[76] Inventors: Klaus Gersonde, Preusweg 69; Hinrich Sick, Lemierserstr. 4, both of D-5100 Aachen, Fed. Rep. of Germany

[21] Appl. No.: 307,504

[22] Filed: Oct. 1, 1981

[30] Foreign Application Priority Data

Oct. 8, 1980 [DE] Fed. Rep. of Germany ....... 3037962

[51] Int. Cl.³ ............................................. G01N 33/48
[52] U.S. Cl. ..................................... 356/41; 356/244; 422/68; 436/68
[58] Field of Search ..................... 356/39, 40, 41, 244, 356/36, 38; 422/68; 436/68

[56] References Cited

U.S. PATENT DOCUMENTS 3,779,708 12/1973 Runck et al. ..................... 356/40 X
4,014,649 3/1977 Kiesow .............................. 356/39 X
4,066,361 1/1978 Achter .................................. 356/41
4,097,921 6/1978 Raffaele ........................... 436/68 X

FOREIGN PATENT DOCUMENTS 1454510 11/1976 United Kingdom .................. 356/36

Primary Examiner—Vincent P. McGraw
Attorney, Agent, or Firm—Ernest F. Marmorek

[57] ABSTRACT

For plotting an equilibrium curve representative of the relation between the oxygen saturation value of a hemoglobin sample, such as blood, and a changing oxygen partial pressure level in a gas, the sample is initially oxygenated by an oxygen-containing gas till it is completely saturated with oxygen, and thereafter by a controlled supply of deoxygenating gas to the volume of gas acting on the sample the oxygen partial pressure is decreased in a controlled manner. The oxygen saturation value is determined from the photometrically measured light absorption parameter of the sample in the measuring space.

12 Claims, 3 Drawing Figures

PROCESS AND APPARATUS FOR PLOTTING THE OXYGEN EQUILIBRIUM CURVES OF BLOOD OR HEMOGLOBIN SOLUTIONS

BACKGROUND OF THE INVENTION

The present invention relates to a method of plotting an equilibrium curve representative of the relation between the oxygen saturation value of a hemoglobin sample (such as blood) and a changing oxygen partial pressure level in a gas, in which the sample is placed in a measuring space, the saturation value being determined from the photometrically measured light absorption of the sample in the space. The invention also relates to an apparatus which is especially designed for carrying out the process according to the invention.

Known ways of plotting equilibrium curves of this type make use of the fact that the absorption properties of hemoglobin undergo changes in the visible light range and in the near IR and UV ranges as a function of the oxygenation of the hemoglobin, that is to say the amount of contained in it. In such a process the blood or other hemoglobin sample is placed as a thin film on a transparent film support so that it may be acted upon by the reaction gas on one side. It is furthermore known in this respect for the sample to be covered on the side acted upon by a the reaction gas by diaphragm which is transparent to light and permeable for the gases in question, such as diaphragm being made for example by PTFE (see K. Schmidt and K. H. Heuser, Z. Respiration 26 (1969), pages (16 to 34), which stabilizes the sample film and prevents the sample from drying up while its properties are being measured.

In a further process of the same general type (see German Auslegeschrift specification No. 2,504,771) an oxygen-containing gas is forced to pass at a low inlet speed into the deoxygenating gas and is agitated or swirled in it.

In all these known ways of testing the "affinity curve" of the oxygen there has been a trend of plotting the equilibrium curve while increasing the oxygen partial pressure. In fact in all cases the sample is initially completely deoxygenated and then at an increasing oxygen partial pressure the increase in the amount of the oxygen combined with the hemoglobin is measured by measuring the level of light absorption, or the relative difference in light absorption.

However, certain problems are encountered in connection with exactly measuring the level of the effective oxygen partial pressure in the measuring space and although the oxygen partial pressure may, as part of a first prior art process, be measured using an oxygen feeler electrode placed in the measuring space, the readings produced are not as exact as might be desired. In a further known measuring operation—the diffusion chamber process—no attempt is made for this reason to directly measure the oxygen partial pressure in the measuring space, and an indirect measuring operation for the oxygen partial pressure is based on the idea of such pressure increasing logarithmically in the measuring space when oxygen is diffusing into the measuring space through a diffusion resistance as for example a diffusion capillary (see H. Sick and K. Gersonde, Analytical Biochemistry 32 (1969), pages 362-376 and 47 (1972) pages 47 to 56). In the case of this process the time needed for a measuring cycle is dependent on the diffusion speed of the oxygen and may not be made arbitrarily as short as desired.

SUMMARY OF THE INVENTION

One purpose of the present invention is that of designing a process of the type initially described which makes it possible for the equilibrium curve to be plotted more quickly and more exactly than in the prior art. More particularly, the readings, and for this reason the findings with respect to the correlation between the oxygen partial pressure and, the oxygen in equilibrium and combined with the hemoglobin, need to be more exact in that part of the equilibrium curve which is most important for the analysis of the equilibrium curve, that is to say especially in the low oxygen partial pressure range.

For effecting this purpose the sample is initially oxygenated by an oxygen-containing gas till it is completely saturated with oxygen and then by a controlled supply of deoxygenating gas to the volume of gas acting on the sample the oxygen partial pressure is decreased more in a controlled manner which, the oxygen dissociation curve is being plotted. More specifically, the sample may be oxygenated to saturation in a first step by using pure oxygen.

Unlike known processes, in the present invention the oxygen level of the reaction gas is decreased, in a controlled manner such a change in the oxygen partial pressure following in general an exponential function so that the decrease takes place at first at a high rate, the rate taking on smaller and smaller values with a decrease in the oxygen concentration. Hence in the physiologically interesting concentration range the partial pressure drop for oxygen takes place slowly and for this reason in this range the equilibrium curve may be plotted very much more exactly than in the known measuring process using enrichment of reaction gas with oxygen, in which, especially in the low concentration range, that is to say in the steep first part of the equilibrium curve, for the reasons touched upon, the changes in concentration take place quickly and for this reason the curve produced will hardly be truly representative at all.

In the measuring method of the present invention, in which the oxygen dissociation curve is measured, on the other hand the change in the partial pressure in the measuring space takes place quickly in the range of high oxygen saturation readings and takes place slowly in the range of low oxygen saturation readings for the blood, so that, for this reason, this part of the curve is stretched out and for this reason may be much more exactly plotted.

In a working form of the invention the measuring space is connected to a gas circulating system, and forms an unchanging volume therewith. This volume or space is filled with pure oxygen before starting the measuring process. The drop in the oxygen concentration is produced by a controlled inlet of deoxygenating gas at atmospheric pressure into the measuring space which at the same time has the function of a mixing space. While the pressure in the measuring space is kept constant at atmospheric pressure the excess gas leaves the measuring space via the bearings and the bore beside the driving shaft g.

Given good and complete mixing of the gas, the decrease in the oxygen partial pressure p may be put in the form of a law:

$$-\frac{dp}{p} = \frac{dV}{V_o} \quad (1)$$

$V_o$ being the unchanging volume of the measuring space and circulating system, while V is the volume of the deoxygenating gas admitted into the measuring space. The solution to the integration of this equation (1) is:

$$\ln p = \ln P_o - \frac{V}{V_o}, \quad (2)$$

or $$p = p_o \cdot e^{-\frac{V}{V_o}} \quad (2a)$$

This mathematical view of the question will make it clear once again that, because of the decrease taking place exponentially of the oxygen partial pressure, the process of the invention provides very much more exact readings in the low oxygen partial pressure range.

Furthermore it is possible, with the help of control undertaken at the same time in line with a given program, for the flow speed of the deoxygenating gas to be so changed as needed that the oxygen dissociation curve is measured or plotted in a way dependent on the volume of deoxygenating gas admitted with the optimum speed, consequently in these ranges, in which there is a small change in the oxygen saturation of the sample, the deoxygenating gas is admitted at a higher speed, the use of an interactive computer electronic system being necessary, so that the computer may additionally be used for the complete processing of the readings and for plotting a curve using normal coordinates.

If one has knowledge of the volume V of deoxygenating gas admitted and of the overall volume of the reaction gas it may be useful to make use, in addition to the oxygenating gas and the deoxygenating gas, of a calibrating gas with a defined oxygen partial pressure, which is responsible for a partial combination of the hemoglobin with oxygen. Along these lines it is possible to obtain a calibration mark on a logarithmic scale, open on its two sides, of the plotter so that it is not necessary to keep on waiting till the last reading is taken for filling the measuring space with the oxygenating gas.

BRIEF DESCRIPTION OF THE DRAWINGS

Further useful effects and details of the invention will be seen from the following description of an apparatus which may more specifically be used for the measuring operation of the invention, as illustrated in the figures, in which.

DESCRIPTION OF THE PREFERRED EMBODIMENTS

Figure 1:
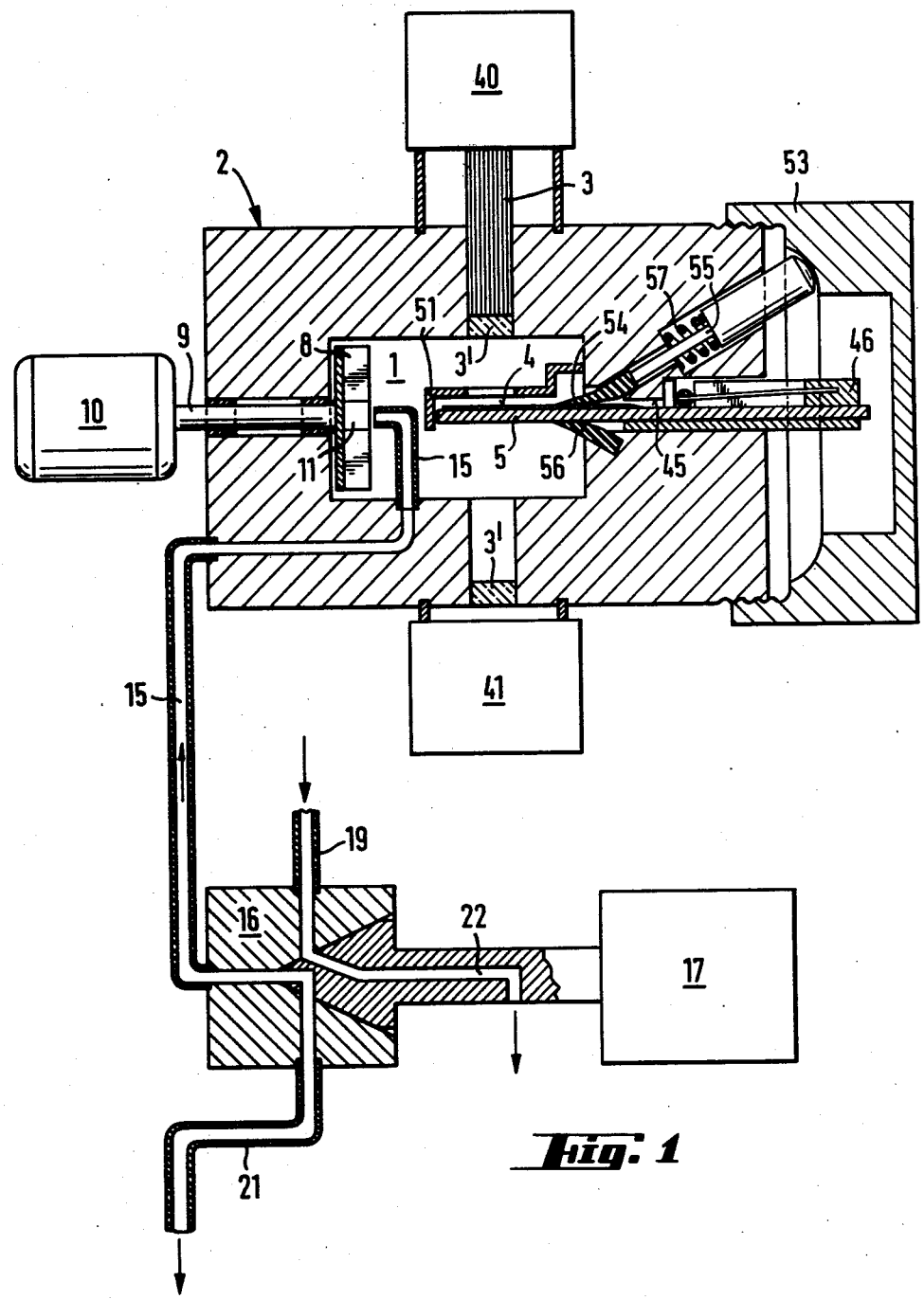
FIG. 1 is a view of a measuring space with the peripheral units in a diagrammatic section.
Figure 2:
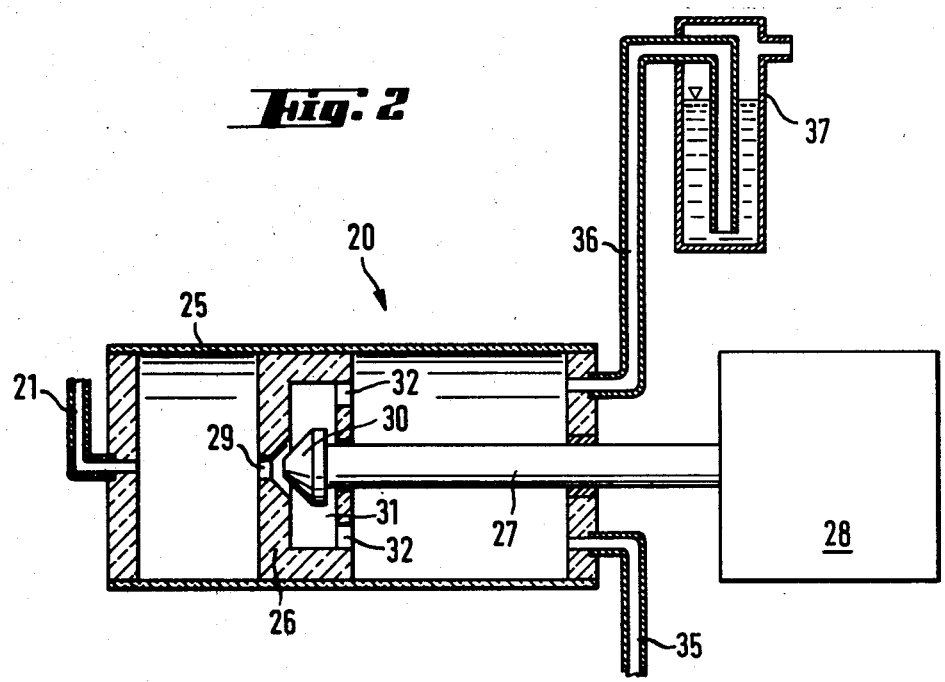
FIG. 2 is a view of an apparatus for controlled inlet of the deoxygenating gas, again in the form of a diagrammatic section.
Figure 3:
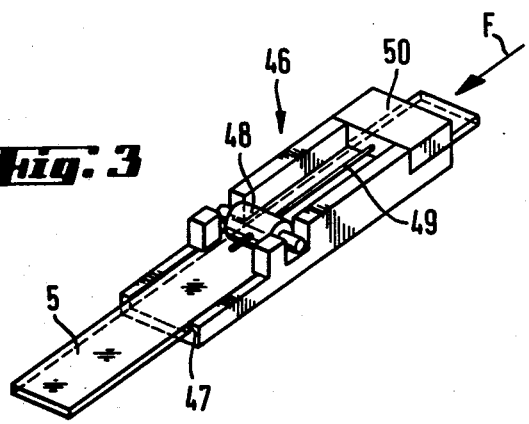
FIG. 3 is a view of the smearing unit, used for the measuring space in FIG. 1, for the blood sample as seen by itself in perspective.

The measuring space 1 is walled in by a housing 2, which at the different inlet pipes and openings has parts for preventing undesired light from passing into the space 1. In the top and lower walls of housing 2 there is in the one case a light guide 3 and in the other case a window 3' so that a measuring beam or ray may pass through the space and through the blood or other hemoglobin sample, which has the form of a thin film or smear 4 on a transparent film support 5.

In the measuring space 1 there is located to one side of the sample an impeller 8 turned by way of the driving shaft 9, journaled in the wall of the housing 2, the driving shaft itself being coupled to a motor 10 which is outside the measuring space 1. Impeller 8 has a central opening 11 and radially extending channels so that for producing a swirling motion of the gas, the gas is forced outwards centrifugally, further gas being admitted through the central opening 11 for the replacement thereof.

Near the central opening 11 there is located an end opening of the inlet pipe 15 for the reaction gas which is to be supplied. Pipe 15 is connected to a two-way valve 16 so that by way of the two-way control 17 the pipe 15 may be connected to the line 19, which is is connected with the oxygenating gas supply system, or (by way of line 21) with the rate controller 20 for the deoxygenating gas. The one or the other gas which is not used in a given case, that is to say not admitted into the measuring space, may be discharged into the outside atmosphere by way of an opening 22. This two-way control system may, in a further operating example of the invention, be used for supplying a calibration gas into the measuring space in addition to the two gases named so far.

The rate controller 20 for the controlled inlet of deoxygenating gas is made up of a glass cylinder 25, in which a piston 26 may be moved backwards and forwards by way of piston rod 27 and a controlled motor driving system 28. Piston 26 is connected to the piston rod 27 so as to move therewith and has a valve opening 29, which may be shut by a closing part 30 placed at the head of the piston rod 27. The hollow space 31 in communication with the valve opening 29, of the piston 26 communicates by way of holes 32 with the space, placed to the back of piston 26, of the glass cylinder 25. When the piston 26 is pushed along by piston rod 27, valve 29, 30 is shut so that the gas volume to the front of piston 26 is forced out of the glass cylinder 25 by way of lines 21 and 15 into the measuring space 1.

To the back of piston 26 line 35 is connected with cylinder 25 and by way of line 35 the deoxygenating gas is supplied. On its other side cylinder 25 communicates by way of line 36 with a pressure limiting valve 37 making certain of a low gage pressure of, for example 5 mbar, in cylinder 25, when piston valve 29, 30 is shut. It is possible for the pressure limiting valve to take the form (see figure) of a pipe extending downwards into a liquid. When piston 26 is moved backwards valve 29, 30 is opened and makes possible free motion therethrough of the deoxygenating gas so that the front part of the glass cylinder 25 is again filled with deoxygenating gas.

The measuring beam or ray is produced by a beam producing system 40 external to the housing 2, the ray being guided by the light guide 3 through the film support 5 and the window 3' onto a beam measuring unit 41. It is best for monochromatic light to be used for the beam, such light having for example a wavelength of 436 nm. Even more exact readings may be produced by using a two-beam system in which the light beam undergoes division into two monochromatic light beams of the same wave length, of which one makes its way through the measuring space while the other is used as a reference beam for monitoring the strength of the monochromatic light using a difference or ratio measuring operation.

Housing 2 has a side opening 45 with a smearing unit 46 therein, unit 46 having a guide 47 passing through the wall of the housing and whose inner size is in line with the cross-section of the film support 5, so that the same may be moved in from the outside through guide 47. Over guide 47 a smearing head 48 is placed so that it may be moved in an upright direction. Smearing head 48 is pushed by spring 49 (fixed in end piece 50) against the film or smear support 5. With the help of this special part of the system the desired blood smear or thin film is produced if it were within the measuring space so that the smeared out sample no longer has any chance of being acted upon by the outside atmosphere and in fact is positioned in the measuring space which has been conditioned beforehand and thus has reached a steady state.

For producing the thin sample film or layer the smearing unit 46 is initially positioned external to the housing 2. Film support 5 is moved in the direction of arrow F right into the guide 47, whereupon a drop of the liquid to be tested is placed on the front end of the film support 5 and thereafter the film support 5 is pulled back till the front end is generally at a position under the smearing head 48 and the smearing unit 46 is pushed into the opening 45. The film support 5 is then slipped in forwards as up to the stop 51 within the measuring space. When this is done the sample is smeared out.

With this system very regular, that is to say reproducible, films may be produced which are about 5 to 50 microns thick, the size of a given film being dependent on the amount of blood or solution placed on the film support and the viscosity thereof. Once the film support 5 has been placed in the measuring space 1, an elastic seal 54, made for example of silicone rubber and which is fixed to a keeper 55 slidingly fixed in the wall of housing 2, is placed against the film support 5, a fixed elastic seal 56 resting against the lower side of the film support 5. Seals 54 and 56 have the function of restraining uncontrolled motion of air into the space 1 by producing a seal at a point at which the film support 5 passes through the housing wall. Keeper 55 is put into operation on putting on the light-tight cover 53 against the urging of the spring 57.

The oxygenating gas used for measuring and the deoxygenating gas and any calibration gas produced are carefully conditioned before being passed into the measuring space and are so enriched with water vapor that the water vapor partial pressure of the gas is in equilibrium with the water vapor pressure of the sample, which prevents any drying of the sample layer and ensures that no wrong readings are produced by any such drying effect. For the purpose of adjustment to attain the correct water vapor partial pressure of the gases it may be best for the enrichment not to be undertaken with pure water but with electrolyte solutions of such a concentration as produce a water vapor pressure over the solution equal to that of the water vapor pressure of the sample, persons skilled in the art having full knowledge of solutions which may be used for water vapor enrichment of the gases and ways in which this may be done. It is naturally necessary before and while readings are being obtained, the measuring space and all parts contacted by the reaction gas of the apparatus have to be carefully conditioned. On taking readings on human blood a temperature of 37° C. will generally be the rule.

By means of the apparatus of which a description has been given the process of the invention, that is to say the way of plotting and analysis of the oxygen dissociation curve may be carried out as follows:

Firstly the apparatus is conditioned and kept at the desired temperature by thermostats. Then oxygenating gas as for example pure oxygen is admitted into the measuring space, the gas having been conditioned and water vapor-enriched. Then the sample is placed in the measuring space as prepared ready for testing. This is accomplished by the film support with one drop of the solution to be tested being pushed past the smearing unit into the measuring space. After sealing off the inlet slot further oxygenating gas is admitted into the measuring space till the sample is completely saturated with oxygen and the measuring space has a defined starting partial pressure $P_o$ of oxygen. The oxygenation of the sample is recorded photometrically using monochromatic light with a wavelength of for example 436 nm. After getting to the so-called saturation condition the conditioned deoxygenating gas is admitted into the measuring space at a controlled rate, the light absorption being recorded at the same time. The curve produced by the plotter is representative of the oxygen dissociation of the sample and has all desired information about the oxygen affinity properties of the sample. In this respect, as part of the invention, the light absorption is measured as a function of the admitted deoxygenating gas volume, that is to say a property or number, which is proportional to the oxygen saturation of the sample, and is recorded on the basis of the admitted deoxygenating gas volume $V \sim \ln p$ or the relative admitted deoxygenating gas volue $V/V_o = \ln p_o = \ln p$.

When the measuring phase has been concluded, deoxygenating gas is admitted at a higher rate for testing to see if the sample is completely deoxygenated.

An interactive microcomputer may be used for automatic control and processing of the readings and for producing, furthermore, an automatic analysis of the oxygen dissociation curve. Such a computer program may be used more specially for producing an analysis of the oxygen dissociation curve in such a way that, taking it that it is a question of physiologically relevant limiting conditions, the oxygen liberating power of the blood is measured. Furthermore other physiochemical properties such as the oxygen half-saturation pressure, the Hill coefficient an the like may be worked out from the readings. It is furthermore possible for a status analysis of the red blood corpuscles to be undertaken with respect to the hemoglobins and effectors present therein by processing the oxygen dissociation curve of a blood sample.

I claim:

1. In a process of plotting an equilibrium curve representing the relation between an oxygen saturation value of a blood or hemoglobin sample in form of a thin film on a light-transparent support as a function of the partial oxygen pressure in a reaction gas supplied to a measuring space, each oxygen saturation value corresponding to a predetermined light absorption parameter of said sample, the steps comprising
   placing said sample into said space,
   oxygenating said sample with an oxygen-containing gas having a predetermined oxygen partial pressure until the sample is substantially saturated with oxygen, thereafter supplying a deoxygenating gas to said space at a controlled rate, so as to decrease said partial oxygen pressure exponentially, determining the partial oxygen pressure on the basis of the amount of deoxygenating gas supplied to said space and mixed with said reaction gas, and simultaneously measuring the light absorption parameter of said sample, whereby said equilibrium curve may be plotted from the oxygen saturation values of said sample corresponding to respective measured light absorption parameters thereof.

2. In a process as claimed in claim 1, wherein said deoxygenating gas is supplied to said space at a constant rate.

3. In a process as claimed in claim 1, wherein said oxygenating step includes a range in which oxygen saturation takes place slowly, and wherein said deoxygenating gas is supplied to said space at variable amounts, so as to decrease said partial oxygen pressure at a higher rate in the range in which said oxygen saturation takes place slowly.

4. In a process as claimed in claim 1, wherein said oxygen containing gas is pure oxygen.

5. In a process as claimed in claim 1, wherein said deoxygenating gas is supplied to said space in such a manner as to swirl the reacting gas contained therein.

6. In a process as claimed in claim 1, wherein said sample has a predetermined water pressure, and said space is at a predetermined temperature, and further comprising the steps of conditioning said reaction gas prior to supplying it to said space so that said reaction gas substantially reaches said predetermined temperature, and of enriching said reaction gas with water vapor until the water vapor pressure thereof is in equilibrium with the water vapor pressure of said sample.

7. In a process as claimed in claim 6, further comprising the step of producing said hemoglobin sample within the conditioned reaction gas.

8. In an apparatus for obtaining an equilibrium curve representing the relation between an oxygen saturation value of a hemoglobin sample as a function of the partial oxygen pressure in a reaction gas, each oxygen value corresponding to a predetermined light absorption of said sample, including a housing, a measuring space defined in said housing arranged to hold a light-transparent support, said light-transparent support being adapted to hold said sample, light generating means adapted to pass a light beam through said sample, light measurement means adapted to measure light values of said light beam following passage thereof through said sample so as to obtain the light absorption parameter of said sample, and arranged to provide a photometric output signal indicative of the measured light values, means for passing the reaction gas to said measuring space, means for decreasing the partial oxygen pressure exponentially in said reaction gas, means for obtaining a signal proportional to said partial oxygen pressure, means adapted to feed said signals to a display unit so as to form and display thereon said equilibrium curve, and means for swirling said reaction gas, in combination said means for swirling said reaction gas including an impeller having a central outlet opening, and wherein said means for passing the reaction gas to said measuring space is a gas inlet line having an outlet aperture disposed near said outlet opening, and said means for obtaining a signal proportional to said partial oxygen pressure including a controlled inlet of deoxygenating gas.

9. In an apparatus for obtaining an equilibrium curve representing the relation between an oxygen saturation value of a hemoglobin sample as a function of the partial oxygen pressure in a reaction gas, each oxygen value corresponding to a predetermined light absorption of said sample, including a housing, a measuring space defined in said housing arranged to hold a light-transparent support, said light-transparent support being adapted to pass a light beam through said sample, light measurement means adapted to measure light values of said light beam following passage thereof through said sample so as to obtain the light absorption parameter of said sample, and arranged to provide a photometric output signal indicative of the measured light values, means for passing the reaction gas to said measuring space, means for decreasing the partial oxygen pressure exponentially in said reaction gas, means for obtaining a signal proportional to said partial oxygen pressure, means adapted to feed said signals to a display unit so as to form and display said equilibrium curve from said signals, and means for agitating said reaction gas, in combination said housing defining a slot, a smearing unit arranged to be received in said slot and including a guide, a film support arranged to be held by said guide, and a smearing head arranged to clamp resiliently said film support, said means for obtaining a signal proportional to said partial oxygen pressure including a controlled inlet of deoxygenating gas, whereby said sample may be obtained from a drop of liquid by placing said drop of liquid on said film support, thereafter shifting said film support under said smearing head until the front end of said film support comes to rest below said smearing head, while passing said smearing unit into said slot, and thereafter shifting said film support into an end position in said measuring space so as to create from said drop of liquid said sample in the form of a thin liquid film.

10. An apparatus as claimed in claim 9, further comprising stop means located within said measuring space for restraining said film support from passing beyond said end position.

11. An apparatus as claimed in claim 9, further including flexible sealing means movable within said housing, but operable for such movement exteriorly thereof so as to form a seal around said film support near said slot, and thereby to protrude partially into said measuring space.

12. An apparatus as claimed in claim 9, further comprising light-tight cover means for covering a portion of said housing defining said slot, so as to prevent any external light from reaching said measuring space.

* * * * *